(12) United States Patent
Ilkov

(10) Patent No.: US 7,564,542 B2
(45) Date of Patent: Jul. 21, 2009

(54) ASYMMETRIC CAPILLARY FOR CAPILLARY-FLOW CYTOMETERS

(75) Inventor: Fedor A. Ilkov, Sunnyvale, CA (US)

(73) Assignee: Guava Technologies, Hayward, CA (US)

( * ) Notice: Subject to any disclaimer, the term of this patent is extended or adjusted under 35 U.S.C. 154(b) by 10 days.

(21) Appl. No.: 11/784,939

(22) Filed: Apr. 10, 2007

(65) Prior Publication Data

US 2007/0236681 A1    Oct. 11, 2007

Related U.S. Application Data

(60) Provisional application No. 60/791,002, filed on Apr. 11, 2006.

(51) Int. Cl.
*G01N 21/00* (2006.01)
(52) U.S. Cl. .......................................... 356/73; 356/246
(58) Field of Classification Search .................. 356/246, 356/73; 204/603
See application file for complete search history.

(56) References Cited

U.S. PATENT DOCUMENTS

| | | | | |
|---|---|---|---|---|
| 5,747,349 | A | * | 5/1998 | van den Engh et al. ..... 436/172 |
| 6,982,787 | B1 | * | 1/2006 | Wapner et al. .............. 356/138 |
| 2004/0053404 | A1 | * | 3/2004 | Grossman et al. ......... 435/287.2 |
| 2005/0089924 | A1 | * | 4/2005 | Ho et al. ...................... 435/7.1 |

OTHER PUBLICATIONS

International Search Report and Written Opinion of International Patent App. No. PCT/US07/66331.

* cited by examiner

*Primary Examiner*—Kara E Geisel
(74) *Attorney, Agent, or Firm*—Leydig, Voit & Mayer, Ltd.

(57) ABSTRACT

The present invention provides improved capillaries that lead to increased resolution in conventional capillary-flow cytometers. The cross-sectional shape of capillaries made according to the present invention lack a center of symmetry. In some embodiments, capillaries have inner side walls that are tilted at angles with respect to the collection-system optical axis so that the widest dimension of the inner bore is closest to the collection optical system and have an outer wall closest to the collection optical system with a dimension large enough to minimize the contribution of outer-wall refraction to the collected light signal. Exemplary capillary embodiments include tubes with a rectangular outer wall and a trapezoidal inner wall, a rectangular outer wall and a triangular inner wall, triangular outer and inner walls, a triangular outer wall with a trapezoidal inner wall, and a hemispherical or rhomboid outer wall and trapezoidal or triangular inner wall.

18 Claims, 11 Drawing Sheets

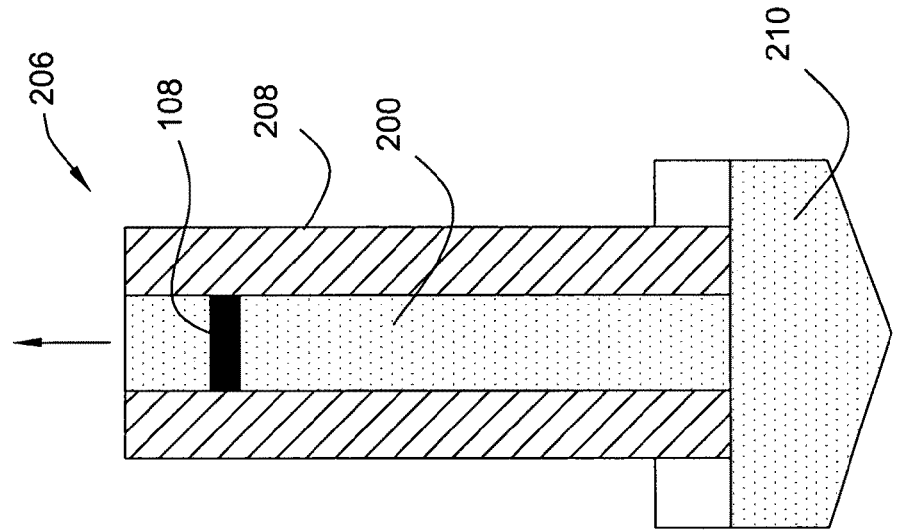
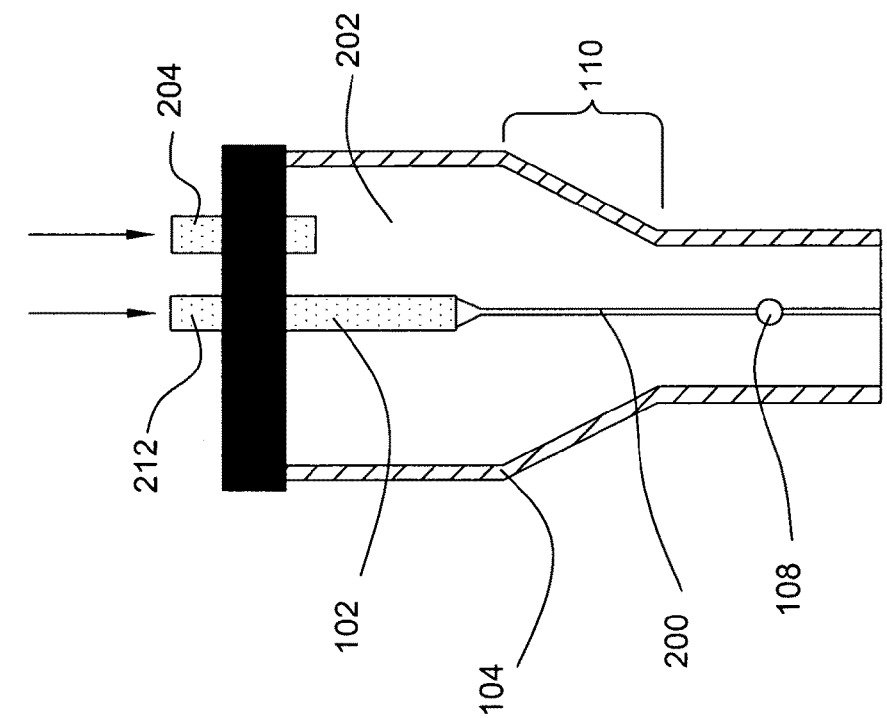

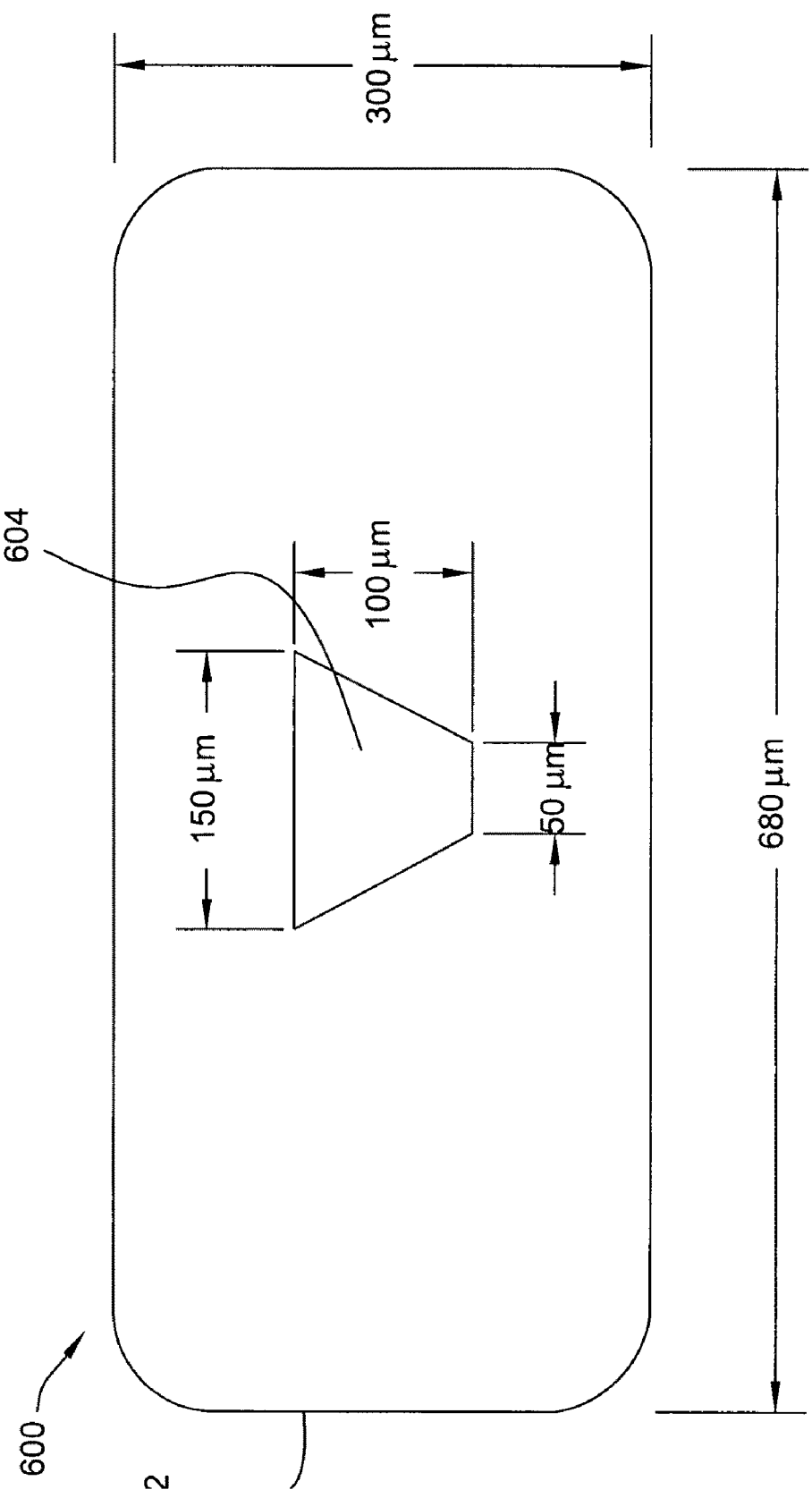

FIG. 8

| Capillary Dimensions | Particle's Position Within the Capillary Bore | | | | | | | Average | CV |
|---|---|---|---|---|---|---|---|---|---|
| | Center | (0, -45 μm) | (0, 45 μm) | (-45 μm, 0) | (45 μm, 0) | (-35 μm, 35 μm) | (35 μm, -35 μm) | | |
| As in Figure 3 | 3.6% | 5.5% | 3.7% | 4.3% | 4.3% | 3.6% | 4.4% | 4.2% | 15.8% |
| Rectangular outer wall (300 μm x 680 μm), square bore (100 μm x 100 μm) | 3.6% | 3.5% | 3.6% | 2.3% | 2.3% | 3.5% | 2.7% | 3.1% | 19.7% |
| As in Figure 6 | 3.57% | 3.55% | 3.59% | 3.58% | 3.58% | 3.59% | 3.55% | 3.57% | 0.5% |

FIG. 9
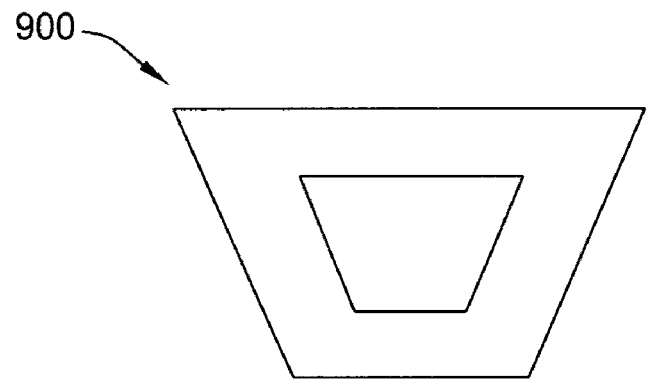
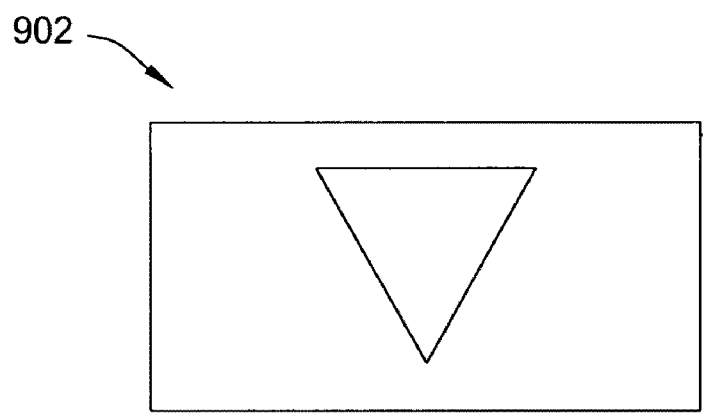
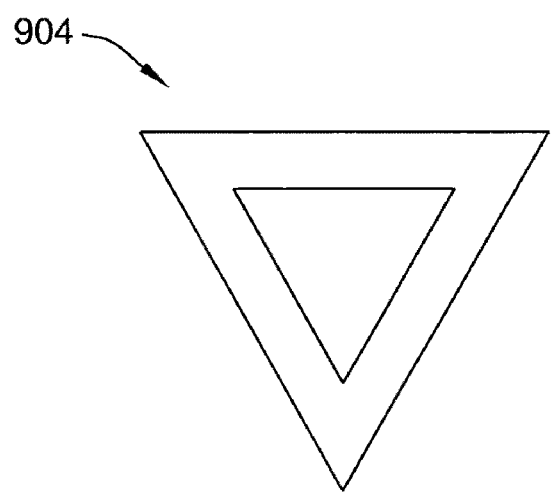

ASYMMETRIC CAPILLARY FOR CAPILLARY-FLOW CYTOMETERS

CROSS-REFERENCE TO RELATED APPLICATION

This application claims priority to U.S. Provisional Patent Application 60/791,002, "Improved Capillary Design for Capillary Flow Cytometers," which was filed on Apr. 11, 2006, and which is incorporated herein by reference in its entirety.

FIELD OF THE INVENTION

The present invention relates generally to flow cytometers for counting particles, and, more particularly, to capillary-flow cytometers.

BACKGROUND OF THE INVENTION

Flow-cytometer systems are used for the detection and counting of micro-organisms and for varied applications throughout the life sciences including clinical diagnostics and immunology, protein and nucleic acid detection, hematology, and oncology. Commercially available instruments range from complex laboratory systems that may be configured for a wide range of measurements to low-cost bench-top systems with more limited capabilities. In the current biotechnology market, the price of a flow cytometer typically increases with its measurement precision and with the number of different measurements it is capable of performing.

Flow cytometers are typically used to identify and count particles with specific characteristics in a fluid sample. In this disclosure, the term "sample particles" may refer, for example, to latex spheres, bacteria, viruses, DNA fragments, cells, molecules, or constituents of whole blood. Sample particles may scatter excitation light directly or may fluoresce when illuminated by light of an appropriate wavelength. In many cases, the fluorescent-emission properties are optimized for specific measurements by attaching probe molecules to the entire sample particles or to microscopic structures within the particles.

In a typical flow cytometer, sample particles are transported by a flowing fluid to an excitation volume where they are illuminated with the focused output beam of a laser or alternative light source. Light that is scattered and emitted by the illuminated sample particles is collected and separated according to emission angle and wavelength using conventional optical systems. Because the sample particles travel through the excitation volume at a high velocity, the light is scattered and emitted in the form of pulses with amplitudes and temporal profiles that are determined by the size and shape of the particles, by their velocity as they pass through the excitation volume, and by the optical characteristics of the light-collection system. In an ideal case, sample particles with the same physical properties produce identical light pulses. In practice, variations in pulse shape are caused by spatially dependent variations in sample particle velocity and in collection efficiency and by the simultaneous illumination of multiple particles.

Light pulses that have been separated according to emission angle and wavelength by the optical system are converted into analog electronic pulses by photomultipliers, solid-state detectors, or alternative light detectors. A data-acquisition system is commonly used to convert the analog signals to a digital data stream for subsequent analysis by a digital signal processor or computer.

The presence of a particular type of sample particle within the excitation volume is determined by comparing the amplitude of the detector pulses to fixed reference levels. Errors in the sample-particle detection process are caused by the simultaneous illumination of multiple sample particles and by variations in the amplitude and shape of pulses that are generated by identical sample particles. The illumination of a single sample particle typically generates a single-peaked detector pulse that is referred to as a singlet pulse. The simultaneous illumination of two sample particles typically generates a detector pulse with two peaks that is referred to as a doublet pulse. In a typical system, the probability of illuminating more than two sample particles is low. Measurement precision and reproducibility are maximized in systems where individual sample particles pass through the excitation volume in a sequential fashion and where identical sample particles produce pulses with the same shape and amplitude.

FIG. 1 is a schematic representation of a conventional sheath-flow cytometer system 100 in which a sample fluid is surrounded by a sheath fluid that may be in the gaseous or liquid state. The sample is injected into the sheath fluid by a core injector 102, and the combined fluids move through a flow tube 104 with a smooth, stationary, laminar velocity distribution that is typically a parabolic function of the radial distance from the flow-tube axis. Particles in the sample fluid interact with light from a focused excitation source 106 within an excitation volume 108 that is downstream from the core injector 102. The diameter of the sample fluid is decreased by gradually reducing the diameter of the flow tube 104 in a neckdown region 110 between the core injector 102 and the excitation volume 108. In the ideal case, the diameter of the sample fluid in the region of the tube 104 containing the excitation volume 108 is small enough that cells (or other sample particles) pass through the excitation volume 108 one at a time. The decreased sample diameter has the added advantages of minimizing radial variations in particle velocity and in optical collection efficiency.

In the cytometer system 100 of FIG. 1, the sheath fluid is introduced into a larger-diameter section 112 of the flow tube 104 through a pressurized inlet 114. The sample fluid is injected into the surrounding sheath fluid through a pressurized core injector nozzle 102 with an axis that is typically coincident with the flow-tube axis. The combined fluids flow through the neckdown region 110 to the excitation volume 108 where the sample fluid is illuminated by a focused excitation light beam that may be generated by a laser, by a laser-driven frequency nonlinear converter such as a frequency doubler, tripler or quadrupler, by an optical parametric oscillator, by a light-emitting diode, by a superluminescent diode, by an arc lamp, or by another light source 106 with a suitable combination of brightness and output wavelength.

An excitation optical system 116 is used to concentrate the excitation beam in the excitation volume 108. The excitation optical system 116 is shown as a simple lens in FIG. 1 but may include one or more components selected from the group of conventional diffractive optics, reflective optics, and refractive optics. An optional bandpass filter 118 with high transmission at the excitation wavelength may be placed between the excitation light source 106 and the excitation volume 108 to block light emitted by the excitation source 106 at wavelengths different from the excitation wavelength.

The focused excitation light interacts with sample particles flowing through the excitation volume 108 via several physical processes including fluorescence excitation, absorption, small-angle scattering, and large-angle scattering. Sample particles are identified and counted by measuring the wavelength, amplitude, duration, and shape of the light pulses that are generated when the moving particles are illuminated by the excitation beam.

Scattered excitation light typically has an angular distribution that is determined by the size and shape of the scattering particles. It is, therefore, advantageous to measure the time-dependent amplitude of the light that is simultaneously scattered at large angles (>45 degrees) and at small angles (<10 degrees) to the excitation-beam propagation axis. Fluorescent light is typically emitted into 4 π solid angle with a distribution that is dependent on the polarization of the excitation light and, possibly, on other factors.

The signal-to-noise ratio is maximized when the fluorescent and scattered light is viewed against a dark background. In large-angle scatter and fluorescence measurements, the background light level is minimized by collecting light at large angles to the excitation-beam propagation direction and using apertures designed to block non-particle scattered light sources. In forward-scattering measurements, the background light level is typically minimized by blocking the excitation beam.

In the cytometer system 100 of FIG. 1, an optical collection system for large-angle light emission 120 gathers fluorescent light and light that is scattered into a cone of angles around an axis that is orthogonal to the excitation-beam propagation axis. Scattered light passes through the dichroic beam splitters 122, 124 and is focused onto the active element of the large-angle scatter detector 126 by a lens 128 or by an alternative focusing optical system. Fluorescent light of a first wavelength is reflected towards a first fluorescence detector 130 by the first dichroic beamsplitter 122, and fluorescent light of a second, different, wavelength is reflected by the second dichroic beamsplitter 124 towards a second fluorescence detector 132. One or more optical bandpass filters 134 are typically placed between the excitation volume 108 and the detectors 126, 130, 132 to restrict the wavelengths reaching each detector 126, 130, 132.

Light that is scattered at small angles to the excitation-beam propagation axis is collected by the forward-scatter imaging system 136. A beam block 138 is typically placed between the excitation volume 108 and the forward-scatter imaging system 136 to prevent the unscattered excitation beam from reaching the forward-scatter imaging system 136. Forward-scattered light passing around the edges of the beam block 138 is collected and focused onto the active element of the forward-scatter detector 140. A bandpass filter 142 is typically inserted between the excitation volume 108 and the forward-scatter detector 140 to transmit light at the excitation wavelength and to block light at other wavelengths.

In the typical sheath-flow cytometer system 100, the excitation volume 108 is defined by the intersection of a tightly focused laser-excitation source and a sample-fluid stream with a typical diameter of a few microns. Light that is scattered and emitted from the sample particles emanates from a small excitation volume 108 that closely approximates a point source.

Fluorescent light is typically generated by probe molecules (organic dye molecules, for example) that are biochemically attached to certain sample particles or to specific structures within certain sample particles before they are introduced into the flow. Probe molecules are typically strong absorbers of excitation light and efficiently convert absorbed light energy to fluorescent emission. A red shift (or Stokes shift) of the fluorescent-light wavelength with respect to the excitation-light wavelength allows the fluorescent light to be separated from the excitation light with a conventional transmission filter or grating. Fluorescent photons are typically emitted within a few nanoseconds after the absorption of a photon from the excitation beam. This delay is short compared to the time required for a particle to travel through the excitation volume 108 in the typical sheath-flow cytometer system 100.

In certain applications, probe molecules with different emission spectra or different excitation spectra may be bonded to different types of sample particles or to different structures within a single type of sample particle. By measuring the amplitude of the fluorescent-light pulses at different wavelengths, it is possible to make simultaneous measurements on a single particle and to differentiate signals that are produced by different sample particles or structures.

Scattered excitation light may be used to discriminate among different sample particle types. The amount of light that is scattered at small angles to the propagation axis of the excitation beam varies with particle size while large-angle scattering increases with particle granularity and with other parameters. Certain particle species may be discriminated by measuring the ratio of small-angle to large-angle scattering.

The shape and amplitude of the light pulses that reach the detectors 126, 130, 132, 140 are determined by the optical properties of the particles, by the particle velocities, by the dimensions of the excitation volume 108, by properties of the light source 106, and by the optical design of the collection optical systems 120, 136 and excitation optical system 116. The optical properties of the particles are dependent on their size, shape, and transparency in addition to the absorption and emission characteristics of any probes that are attached to the particles. Strongly absorbing probes with a high quantum yield for fluorescent emission typically generate pulses of maximum amplitude.

In a typical application, at least one detector 126, 130, 132, 140 receives a light pulse when a particle is illuminated by the excitation beam. Each interaction between a particle and the excitation beam is known as an "event." In the ideal case, a particle can be identified from the characteristics of the detector pulses that are generated during an event. For example, it is possible to count and to discriminate among monocytes, granulocytes, and lymphocytes in a sample by measuring the relative magnitude of the small- and large-angle scattering signals. Errors are introduced into the particle-identification process by deviations from smooth laminar flow, by spatial variations in particle velocity and collection efficiency, and by the simultaneous illumination of multiple particles.

In a typical capillary tube, the flow velocity has a parabolic distribution with the greatest velocity in the tube center. The parabolic distribution is nearly flat (radial derivative near zero) near the tube axis, and particles traveling in a region near the axis have approximately the same velocity. In capillary-flow cytometers, particles traveling near the wall of the tube have a significantly lower velocity and produce longer pulses than those traveling near the center. Deviations from the laminar-flow condition (turbulent flow) lead to unpredictable, time-dependent pulse-shape variations.

While the vast majority of commercial and research flow cytometers utilize a sheath-flow cell as shown in FIG. 1 and described above, some flow cytometers (e.g., those manufactured by Guava Technologies) are based on an alternative, and simpler, flow-cell design in which the sample fluid completely fills a square capillary cell. FIGS. 2A and 2B are cross sections of representative sheath-flow and capillary-flow cells, respectively. Conventional sheath-flow cytometers are described, for example, in U.S. Pat. Nos. 4,662,742 and 4,745,285. A state-of-the-art capillary-flow system is described in U.S. Patent Publication 2002/0028434 A1.

In the sheath-flow cell of FIG. 2A, the particle-containing sample fluid 200 is confined to a region near the capillary axis by a clear sheath fluid 202. As described above, the sample 200 is introduced into the sheath fluid 202 by a specially designed core injector 102, and the two fluids 200, 202 flow through the cell under a positive pressure provided by the sheath-fluid 204 and sample-fluid 212 inlets. Between the core injector 102 and the excitation volume 108, the combined sheath 202 and sample 200 fluids travel through a tapered, neckdown region 110 where the flow cross-section is reduced. This reduction in the diameter of the flow-tube 104 increases the flow velocity and reduces the diameter of the sample 200 and sheath 202 fluids. Typical diameters for the sample fluid 200 in the excitation region 108 of a sheath-flow cytometer system 100 are in the range of 2 µm to 25 µm, while the diameter of the sheath fluid 202 is typically greater than 100 µm.

In the capillary-flow system 206 of FIG. 2B, there is no sheath fluid, and the sample fluid 200 and the excitation volume 108 fill the entire cross-section of the capillary 208. The sample fluid 200 is drawn from a sample reservoir 210 by a pump (not shown) on the downstream end of the capillary 208 and pumped through the excitation volume 108. Sample particles emit and scatter light at all points throughout the cross-section of the capillary 208. The cross-sectional dimension of the sample fluid 200 in the excitation region 108 is significantly larger than the cross-sectional dimension of the sample fluid 200 in the sheath-flow system 100. For example, a typical inside edge dimension for a square capillary 208 in a capillary-flow cytometer is 100 µm.

In general, conventional sheath-flow cytometers 100 have the following performance advantages when compared to capillary-flow cytometers:

(1) The variation in flow velocity in the excitation volume 108 is small. The sample fluid 200 is restricted to a region of the parabolic flow-velocity distribution where the first derivative of the particle velocity is small. This is in contrast to a capillary-flow system where particles flow through the entire cross section of the capillary 208.

(2) Variations in optical-collection efficiency are small. Because the sample fluid 200 is confined to a small region near the flow-tube axis, the excitation volume 108 typically acts like a fixed point source, and wall effects have a negligible effect on pulse amplitude. This is in contrast to conventional capillary-flow instruments where wall effects typically cause significant, position-dependent variations in pulse amplitude.

(3) The smaller excitation volume 108 in sheath-flow instruments makes it possible to use a collection lens with a higher numerical aperture. It also reduces the background noise level and the probability of simultaneously illuminating multiple particles.

For many measurements, however, capillary systems provide adequate measurement accuracy and offer the following advantages over sheath-flow systems 100:

(1) Capillary systems are cheaper and less complex. Sheath-flow cells are complex, expensive, and difficult to align properly. Capillary-flow cells are simpler, cheaper, and less prone to misalignment.

(2) The sample fluid 200 is drawn through the capillary 208 by a pump, thereby facilitating the direct measurement of particle concentration in the sample fluid 200. In a sheath-flow cytometer 100, the sample 200 and sheath 202 fluids are injected into the flow tube 104 under pressure, and particle concentrations are typically measured indirectly by introducing a sample fluid 200 with a known particle concentration into the system.

(3) The sheath fluid 202 and associated fluidics are eliminated The simpler fluidics of a capillary-flow instrument offer significant cost savings for certain common measurements where reductions in measurement accuracy are acceptable.

According to Shapiro (Practical Flow Cytometry, 4$^{th}$ Edition, Wiley, Hoboken, 2003), "the measurement precision of a cytometer is routinely characterized by accumulating a distribution of measured values of fluorescence or light scattering intensities from 'nearly identical particles' and computing the coefficient of variation (CV), which, expressed as a percentage, is 100 times the standard deviation for the measurement divided by the arithmetic mean, or average." Smaller CVs are associated with increased accuracy.

In a typical measurement, a count is increased whenever the amplitude of a pulse from a detector exceeds a predetermined threshold value. Variations in the pulse amplitudes produced by identical particles lead to counting errors and thus to an undesirable increase of the CV for a measurement. CVs in conventional capillary-flow cytometers typically exceed those of sheath-flow instruments 100 because of the capillary-flow cytometers' larger excitation volumes 108 and because of the emission of light from particles far removed from the capillary axis.

The CVs for measurements made with a capillary-flow cytometer may be improved by concentrating the sample particles in a small region near the capillary axis. U.S. Pat. No. 6,710,871, for example, describes a capillary-flow cytometer system in which a magnetic field is used to force magnetically-charged particles to flow within a restricted cross-sectional area of the capillary 208.

The CVs of measurements made with a capillary-flow cytometer may also be improved (that is, decreased) through the use of digital signal-processing algorithms for the determination of pulse velocity and the real-time identification of pulses that are generated by the simultaneous illumination of two or more particles. In comparison to sheath-flow instruments 100, the probability of simultaneously illuminating two particles is increased due to the larger excitation volume 108. Improved doublet detection in capillary-flow instruments may be accomplished by applying a combination of velocity-determining algorithms and conventional, sheath-flow methods as outlined in "Doublet Discrimination in DNA Cell-Cycle Analysis," by R. P. Wersto, et. al., Cytometry, 46:296-306 (2001).

The optical collection system for large-angle light emission that is used in a conventional capillary-flow cytometer collects light that is emitted or scattered into a cone of angles about the collection-system axis. Reflection and refraction of light by the walls of the flow tube typically lead to the collection of different amounts of light from identical particles that are excited at different points within the flow tube. Variations in the amount of collected light lead to variations in the amplitude or shape of the electronic pulses produced by the detectors and thus to an increase in the CVs for measurements made with the instrument.

In principle, the excitation volume 108 could be reduced by using a capillary 208 with a smaller bore, but a reduction in the diameter of the capillary 208 leads to an increased probability that sample particles will clump together and clog the capillary 208. Capillary clogging is fatal to any measurement and places a practical lower limit on the bore dimension of a square capillary 208 that is determined by the size of the particles.

Economical and efficient methods for reducing wall effects are unknown in the prior art.

BRIEF SUMMARY OF THE INVENTION

In view of the foregoing, the present invention provides improved capillaries for use in capillary-flow cytometers. The cross-sectional shape of capillaries made according to the present invention lack point symmetry. This significantly reduces position dependent variations in pulse shape and amplitude caused by scattering and refraction of light by the capillary walls. The shape of the outer and inner capillary walls lowers (improves) the measured CV.

In some embodiments, capillaries have inner side walls that are tilted at angles with respect to the collection-system optical axis so that the widest dimension of the inner bore is closest to the collection optical system and have an outer wall closest to the collection optical system with a dimension large enough to minimize the contribution of outer-wall refraction to the collected light signal. The position-sensitive variation in collected light and the associated contribution to measured CV can be minimized by selecting the inner-wall tilt angle and outer-wall dimension according to the numerical aperture and field-stop diameter of the collection optical system.

Exemplary capillary embodiments include tubes with a rectangular outer wall and a trapezoidal inner wall, a rectangular outer wall and a triangular inner wall, triangular outer and inner walls, and a triangular outer wall with a trapezoidal inner wall. Some capillaries have hemispherical or rhomboid outer walls and trapezoidal or triangular inner walls.

Further embodiments of the invention minimize the amount of scattered excitation light entering the collection optical system by having wall dimensions in the direction parallel to the collection axis that are large enough to minimize interactions between the excitation beam and the outer wall.

BRIEF DESCRIPTION OF THE SEVERAL VIEWS OF THE DRAWINGS

While the appended claims set forth the features of the present invention with particularity, the invention, together with its objects and advantages, may be best understood from the following detailed description taken in conjunction with the accompanying drawings of which:

FIG. 2A is a cross-sectional view of the nozzle and excitation volume of a typical sheath-flow cytometer;

FIG. 2B is a cross-sectional view of the flow tube and excitation volume of a typical capillary-flow cytometer;

FIG. 6 is a cross-sectional view of an exemplary capillary lacking point symmetry according to the present invention;

FIG. 8 is a table comparing the percentage of light captured in a capillary-flow cytometer when using three different capillaries; and FIG. 9 shows cross-sectional views of three exemplary capillaries lacking point symmetry according to the present invention.

DETAILED DESCRIPTION OF THE INVENTION

Figure 1:
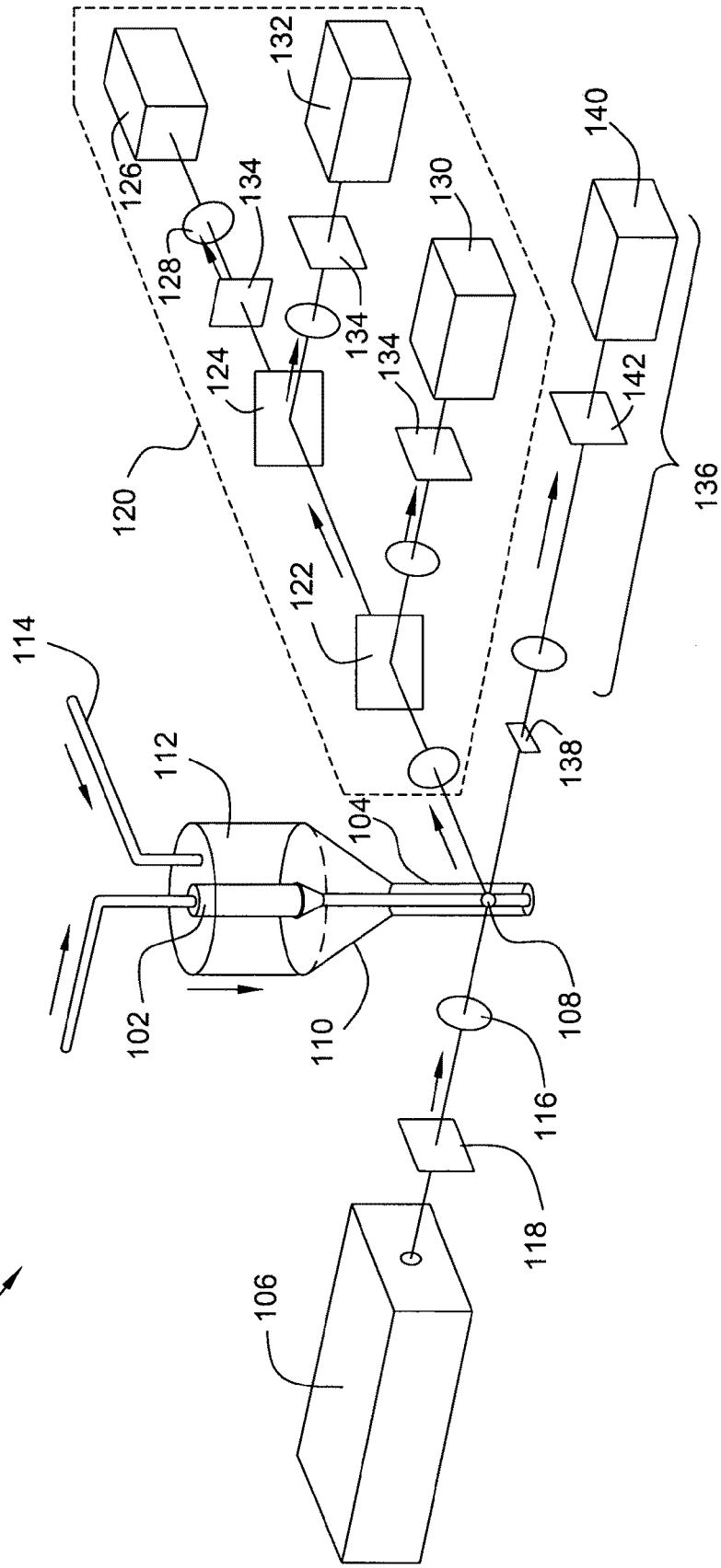
FIG. 1 is a schematic diagram of a conventional sheath-flow cytometer system from the prior art.

Turning to the drawings, wherein like reference numerals refer to like elements, the present invention is illustrated as being implemented in a suitable environment. The following description is based on embodiments of the invention and should not be taken as limiting the invention with regard to alternative embodiments that are not explicitly described herein.

Position-dependent variations in pulse shape and in amplitude caused by scattering and refraction of light by the capillary walls in prior art capillary-flow cytometers may be significantly reduced through the use of improved capillary designs. In contrast to the square and round capillaries of the prior art, the cross-sectional shapes of the improved capillaries lack point symmetry. The replacement of a conventional square capillary with an asymmetric capillary embodying the present invention minimizes wall effects. CVs for fluorescent counting measurements performed by capillary-flow cytometers incorporating the improved capillaries are expected to be principally limited by volume effects due to doublet and background light rather than by wall effects. The improved devices attain CVs approximately less than two times larger than those obtained with conventional sheath-flow cytometers. This performance may be contrasted to conventional capillary-flow instruments with CVs that are five to ten times greater than the CVs of sheath-flow instruments.

Embodiments of the present invention may advantageously be mass-produced using wafer-scale techniques that are known in the prior art. For example, capillaries with a wide range of inner-bore geometries may be manufactured using high precision powder blasting and optical bonding techniques, photolithography, glass molding, and stamping. They may also be produced using conventional glass-drawing techniques.

Figure 3:
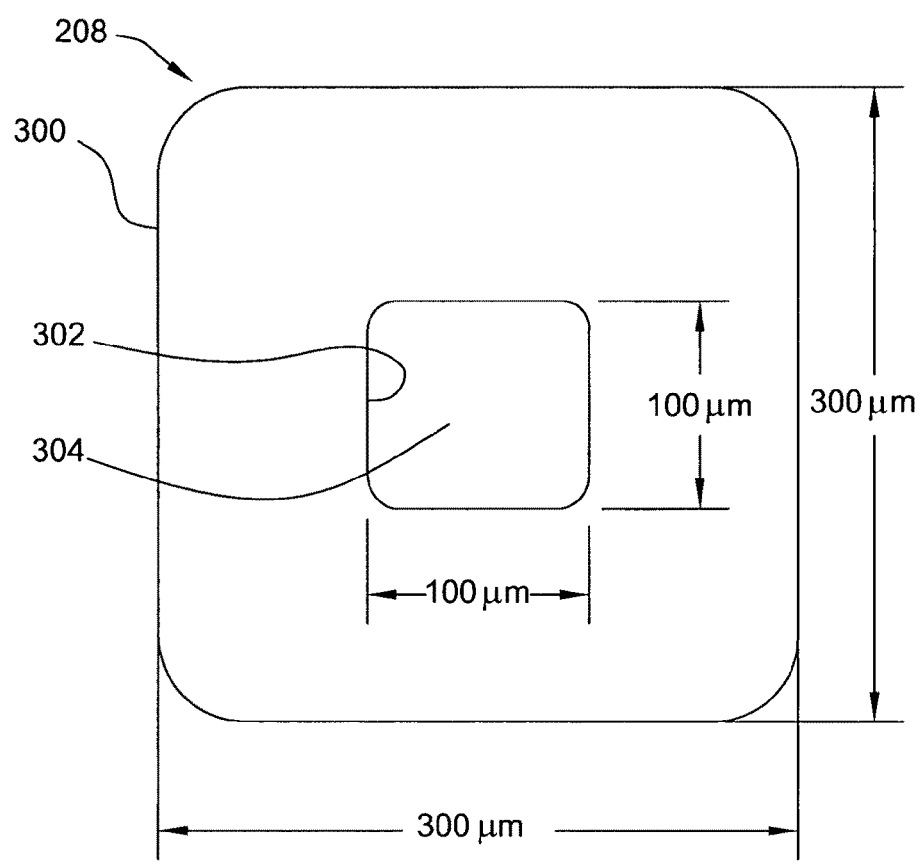
FIG. 3 is a cross-sectional view of a conventional square capillary.

To illustrate the inherent limitations of the prior art symmetric capillary designs, consider the representative square capillary 208 shown in FIG. 3. This square capillary 208 is similar to those used in Guava Technologies' commercial capillary-flow cytometers. As seen in the Figure, both the outer side wall 300 and the inner side wall 302 (which defines the bore 304 of the capillary 208) are roughly square.

Figure 4:
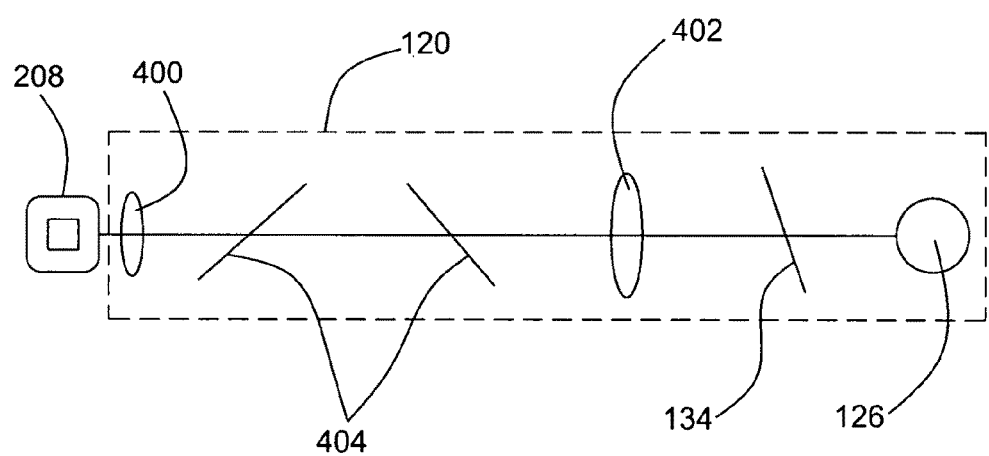
FIG. 4 is a schematic diagram of an exemplary optical collection system for large-angle light emission.

Fluorescent emission from sample particles in the capillary 208 of FIG. 3 may be imaged into a single photomultiplier-tube detector 126 with the representative optical collection system for large-angle light emission 120 of FIG. 4. In this system, light is collected by an AR-coated, molded glass aspherical lens 400 that has a numerical aperture of 0.50 and an effective focal length of 8.00 mm. The aspherical lens 400 is typically positioned at a distance of 5.8 mm from the wall of the capillary 208. The distance from the aspherical lens 400 to the photomultiplier-tube detector 126 is approximately 150 mm. A relay lens 402 is positioned approximately 90 mm from the aspherical lens 400. The system performance is unaffected by the position of the longpass filters 404 and by the position of the bandpass filter 134. In addition to the representative optical system of FIG. 4, light from capillaries according to the present invention may be collected using alternative optical systems known in the flow-cytometry art.

FIGS. 5A through 5G illustrate light collection from identical fluorescent particles that are located at different positions within the bore 304 of the square capillary 208 of FIG. 3. The particles are identically illuminated in each figure. In the following table, a particle's position is specified with respect to a rectangular coordinate system that has an origin located at the center of symmetry of the capillary 208. The x-axis is directed horizontally, parallel to the outer side wall 300 of the capillary 208, and the y-axis is directed in the orthogonal, vertical direction. The focal line of the excitation beam is coincident with the y-axis of the coordinate system. Individual ray paths are shown as lines in FIGS. 5A through 5G, and the collected rays are shaded gray.

| FIG. | Particle's Position Within the Capillary Bore |
|---|---|
| 5A | Center: (0, 0) |
| 5B | (0, −45 μm) |
| 5C | (0, 45 μm) |
| 5D | (−45 μm, 0) |
| 5E | (45 μm, 0) |
| 5F | (−35 μm, 35 μm) |
| 5G | (35 μm, −35 μm |

Figure 5A:
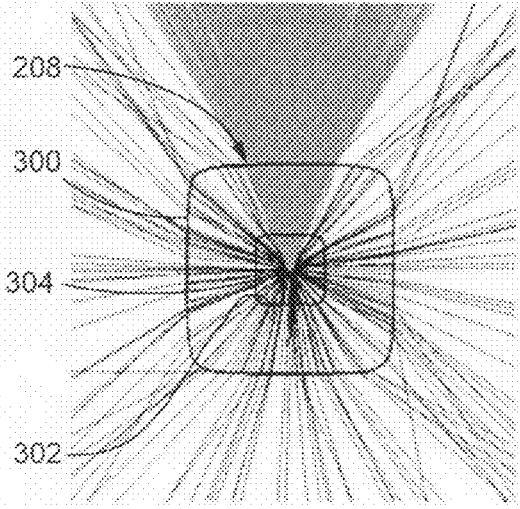
FIGS. 5A through 5G are schematic diagrams of light collection from particles at various positions within a square capillary.

In FIG. 5A, the particle is located at the center of the bore 304 of the square capillary 208. Rays are emitted in all directions and are refracted by the air-glass interface at the outer side wall 300 of the capillary 208. Refraction at the interface between the sample and the inner side wall 302 of the capillary 208 is negligible because the difference in the refractive indices is small. Rays that are shaded gray at the top of FIG. 5A are collected by the molded glass aspherical lens 400 (see FIG. 4) and are directed to one or more detectors 126. A significant feature of light collection from a point at the center of the capillary 208 is the straightforward effect of refraction at the air-glass boundary: This refraction narrows the cone of collected rays within the capillary 208, effectively decreasing the numerical aperture of the collection optical system 120 (see FIGS. 1 and 4).

FIGS. 5B through 5G show light collection from particles that are displaced from the center of the bore 304 of the capillary 208. A careful examination of FIGS. 5B through 5G shows that the amount of light collected from these off-axis points is influenced by two effects:

(1) refraction at the air/glass boundary at the outer side wall 300 of the capillary 208 and (2) small-angle reflection at the interface between the sample and the inner side wall 302 of the capillary 208.

Compared to an on-axis emitter, outer-wall refraction leads to an increase in the number of rays of light collected from certain off-axis points, while reflection from the inner side wall 302 decreases the number of collected rays. The relative magnitude of these effects and their ultimate effect on measured CV are functions of the optical system numerical aperture, the field-stop diameter, and the shape of the capillary 208. The position-dependent variation in the number of collected rays has a deleterious effect on the precision of a capillary-flow cytometer. Variations in collection efficiency increase the standard deviation for measurements performed on identical particles and deleteriously increase the CV.

According to the present invention, the measured CV may be minimized by changing the shape of the inner and outer side walls of the capillary. The optimal capillary dimensions depend on the numerical aperture and field-stop diameter of the collection optical system. In some embodiments of the present invention, capillaries have inner side walls that are tilted at angles with respect to the collection system optical axis so that the widest dimension of the inner bore is closest to the collection optical system. In addition, the capillary's outer side wall closest to the collection optical system has a dimension large enough to minimize the contribution of outer-wall refraction to the collected light signal. The position-sensitive variation in collected light and the associated contribution to the measured CV may be advantageously minimized by selecting the inner wall tilt angle and the outer wall dimension based on the numerical aperture and field-stop diameter of the collection optical system.

FIG. 6 shows an improved capillary 600 embodying aspects of the present invention. The capillary 600 minimizes the positional variation in the amount of light scattered or emitted by sample particles and collected by an optical system with a numerical aperture of 0.5. The capillary 600 has a rectangular outer side wall 602 that is 680 μm wide in the x-axis direction and 300 μm wide in the y-axis direction. The cross section of the inner bore 604 is trapezoidal, and the bore 604 is centered within the rectangular outer side wall 602. The long side of the trapezoid measures 150 μm, and the short side is 50 μm long. The, long and short sides are separated by a perpendicular distance of 100 μm.

Figure 5B:
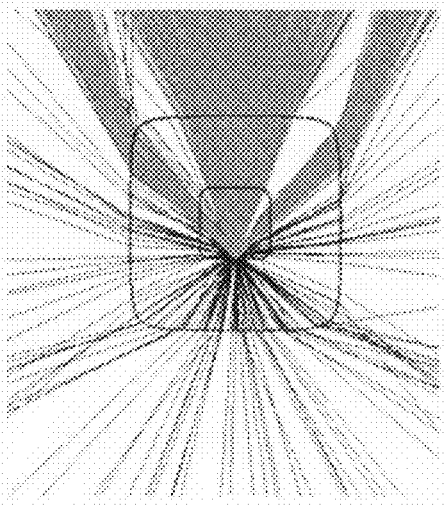
Figure 5C:
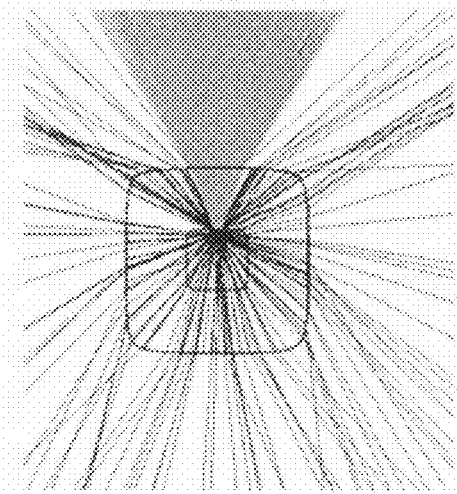
Figure 5D:
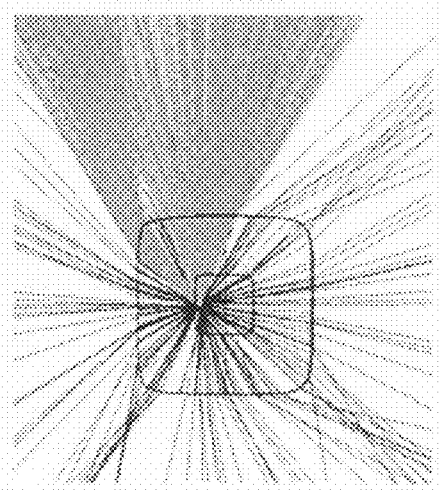
Figure 5E:
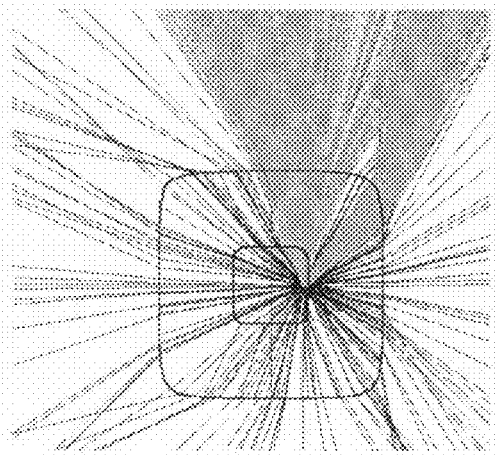
Figure 5F:
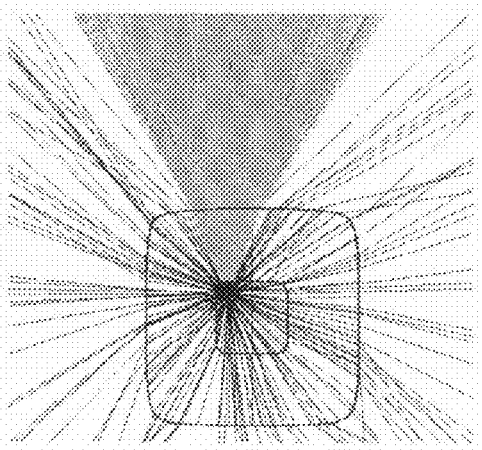
Figure 5G:
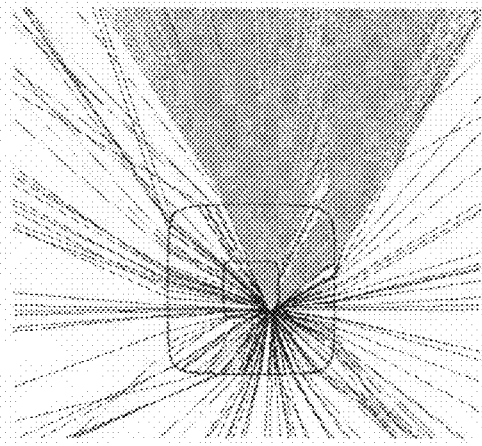
Figure 7A:
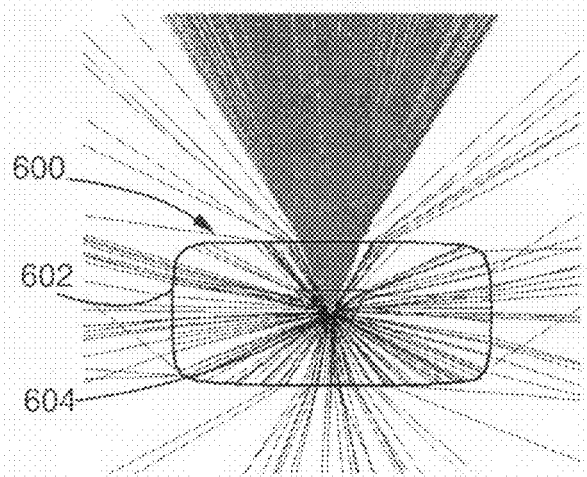
FIGS. 7A through 7G are schematic diagrams of light collection from particles at various positions within the exemplary capillary of FIG. 6.
Figure 7B:
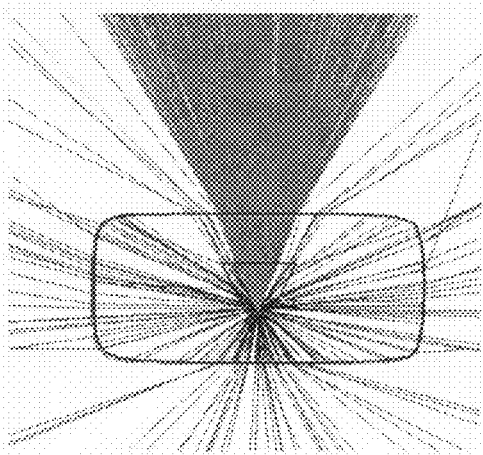
Figure 7C:
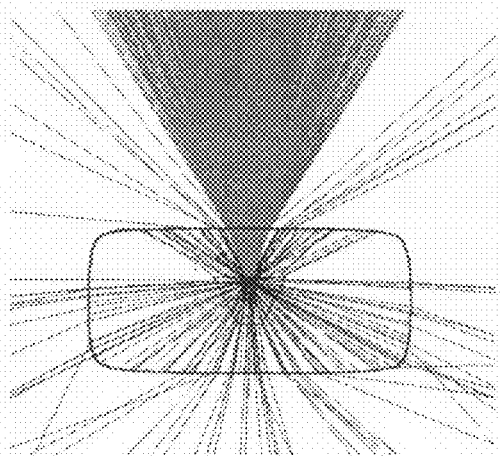
Figure 7D:
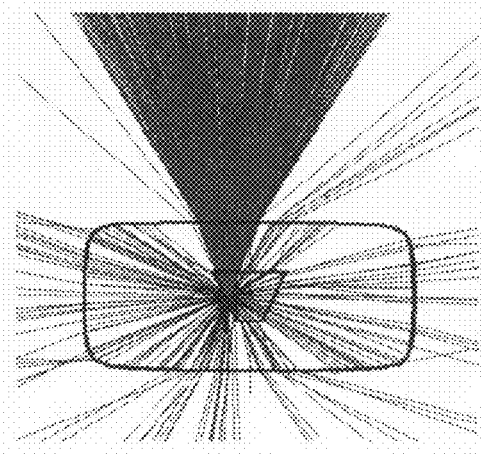
Figure 7E:
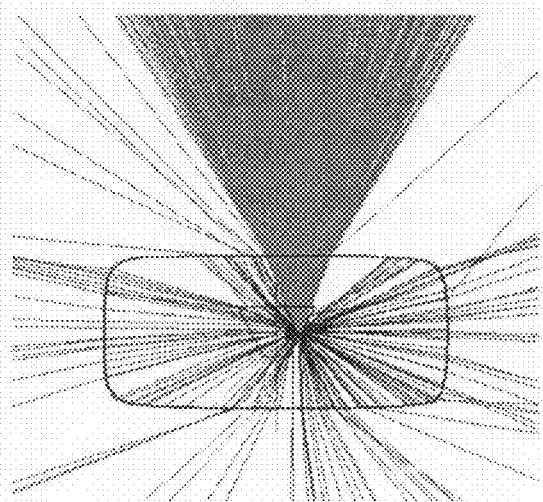
Figure 7F:
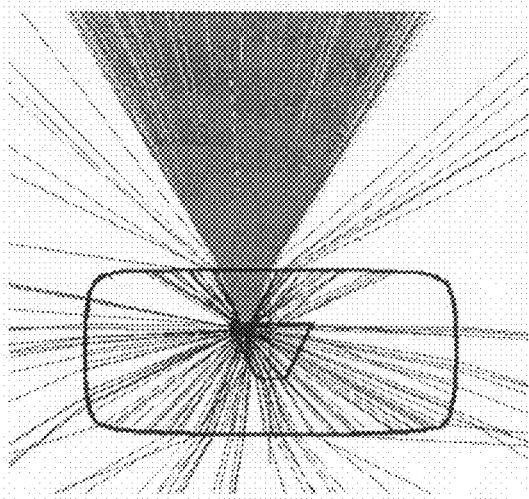
Figure 7G:
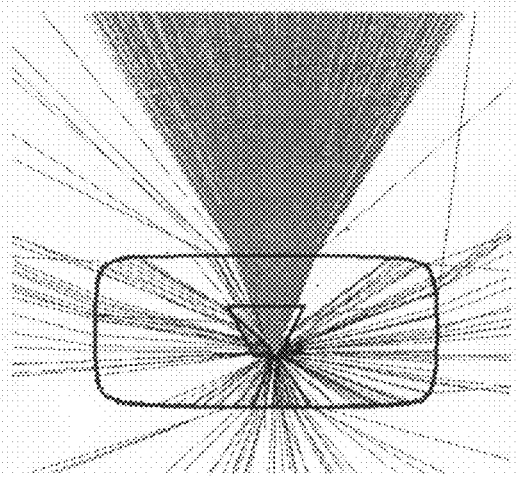

FIGS. 7A through 7G show light collection from identical particles that are displaced from the center of the bore 604 of the capillary 600 of FIG. 6 by distances equal to those in FIGS. 5A through 5G, respectively. (See Table below.) The effects of outer-wall refraction and of small-angle reflection are significantly reduced by the trapezoidal embodiment and by the rectangular outer wall shape. In particular, compare FIGS. 5B and 7B. In FIG. 5B, light refracted from the side faces of the capillary 208 is directed toward the optical collection system (not shown but toward the top of FIG. 5B). In contrast, in FIG. 7B the extended face of the capillary 600 that is closest to the optical system prevents this light from reaching the optical collection system. The result is that substantially all light reaching the optical collection system in FIGS. 7A through 7G passes through this front face of the capillary 600. Here, "substantially all" means that 75% or more of the light that reaches the optical collection system passes through the front face of the capillary 600. Higher percentages are preferable and, in some embodiments, the percentage exceeds 90%.

| FIG. | Particle's Position Within the Capillary Bore |
|---|---|
| 7A | Center: (0, 0) |
| 7B | (0, −45 μm) |
| 7C | (0, 45 μm) |
| 7D | (−45 μm, 0) |
| 7E | (45 μm, 0) |
| 7F | (−35 μm, 35 μm) |
| 7G | (35 μm, −35 μm |

FIG. 8 summarizes the results of numerical ray-tracing calculations for light-collection efficiency in FIGS. 5A through 5G (top row) and in FIGS. 7A through 7G (bottom row) under the assumptions that the particles are uniformly distributed inside the capillaries and that the capillaries are identically illuminated. The center row summarizes the results of an additional calculation for the case of a capillary with a square inner bore and a rectangular outer bore. Columns 2 through 8 show the percentage of light collected by an optical system from particles at different positions inside the bore. Column 9 shows the average of columns 2 through 8, and column 10 shows the value of the CV calculated from data in the other columns. Comparing the bottom row with the other two rows, the variation in collected light and the corresponding CVs are significantly reduced by the capillary 600 made according to aspects of the present invention.

Conventionally, the measured CVs of a prior art capillary cytometer with a square capillary may be reduced by placing apertures in the collection optical system to block a portion of the side-wall refracted light. Unfortunately, the insertion of corrective apertures has the undesirable effect of reducing the amount of light collected, thereby reducing the sensitivity. Aperture-corrected systems impose tighter dimensional tolerances on the capillary and are sensitive to the relative position of the aperture and capillary, often requiring active alignment for optimal results. In the best case, the CVs of the measurements made with an aperture-corrected capillary-flow cytometer are two to three times greater than the theoretical CVs of measurements made with a capillary-flow instrument incorporating the trapezoidal embodiment of FIG. 6.

While offering significant improvements in the performance of the optical collection system for large-angle light emission, the embodiment of FIG. 6 has little effect on sample excitation and on the measurement of small-angle forward scatter. There is negligible refraction at the small index step at the inner sample/glass interface. The contributions of reflection at the inner wall and refraction at the outer wall on the amount of light reaching the forward scatter detector are comparable in magnitude to those observed in a conventional square capillary.

Some alternative embodiments of the invention share the following properties with the FIG. 6 embodiment.

(1) The dimension of the outer wall in the direction perpendicular to the axis of the optical collection system for large-angle light emission is chosen in such a way that signal contributions from outer-side-wall refraction and corner refraction are minimized.

(2) The inner side walls are angled with respect to the collection system axis to minimize the contribution of small-angle reflection and the corresponding position-sensitive variations in the collected light signal. The magnitude of the inner-side-wall angle is dependent on the numerical aperture of the collection optical system, being greater than 20 degrees for a system with a numerical aperture of 0.5 and greater than 5 degrees for a system with a numerical aperture of 0.1.

A few alternative embodiments incorporating these design principles are shown in FIG. 9. They include designs with trapezoidal outer and inner walls (900), a rectangular outer wall and a triangular inner wall (902), and triangular outer and inner walls (904). These alternatives are not exclusive but should be considered representative of capillary designs embodying the present invention.

Further embodiments of the invention minimize the amount of refracted excitation light entering the collection optical system by having wall dimensions in the direction parallel to the collection axis that are large enough to minimize interactions between the excitation beam and the outer wall. For example, with an illuminating laser beam diameter of 0.7 mm at the 1/e power points, background light levels may be minimized by capillary designs in which the dimension of the outer capillary wall in the direction parallel to the large-angle collection axis is greater than 0.7 mm. Advantageously, the amount of background light reaching the detector may be further reduced by decreasing the area of the inner bore to the limit imposed by clogging.

Capillaries embodying the features of the present invention may be mass-produced using wafer-scale techniques. Such techniques are, for example, practiced commercially by Anteryon B V, P.O. Box 33, 5600 AA Eindhoven, The Netherlands. To fabricate the capillary 600 of FIG. 6, for example, a large number of trapezoidal bores are fabricated in a first glass plate using Anteryon's high precision powder blasting techniques. After the trapezoidal shapes are formed in the first plate, hollow, trapezoidal cores are formed by bonding the first plate to a second glass plate. The thickness of the bonded plates is chosen in such a way that the core position and thickness in the y-direction match those in FIG. 6. Appropriate dimensions in the x-direction are obtained by sawing the bonded plates. Using these techniques, a large number of capillaries are fabricated in a single process, thereby minimizing the cost of an individual capillary. This method of capillary manufacture allows the fabrication of a wide range of different core geometries and could be modified to form structures that require the blasting of both plates.

In view of the many possible embodiments to which the principles of the present invention may be applied, it should be recognized that the embodiments described herein with respect to the drawing figures are meant to be illustrative only and should not be taken as limiting the scope of the invention. Those skilled in the flow-cytometry or optical-fabrication arts will realize that the invention may be practiced using capillary designs other than those shown in FIGS. 6 and 9. Such capillary designs would simultaneously reduce the contributions of outer-wall refraction and inner-wall reflection to the large-angle collected light signal but may have alternative outer- and inner-wall geometries. For example, capillaries with hemispherical or rhomboid outer walls and trapezoidal or triangular inner walls clearly embody the features of the invention. Therefore, the invention as described herein contemplates all such embodiments as may come within the scope of the following claims and equivalents thereof.

I claim:

1. A capillary for use in a capillary-flow cytometer, the capillary comprising:
   a wall defining a bore extending in a longitudinal direction, the wall further comprising:
   a substantially non-reflective inner wall surface defining a cross-sectional shape of the bore, the cross-sectional shape of the bore being traverse to the longitudinal direction of the bore and lacking point symmetry; and
   an outer wall surface defining a cross-sectional shape of the wall that is traverse to the longitudinal direction;
   wherein the cross-sectional shape of the wall is the same as the cross-sectional shape of the bore; and
   wherein the capillary is configured so that upon installation in a capillary-flow cytometer, substantially all light collected by an optical collection system of the capillary-flow cytometer passes through a side of the outer wall surface that is closest to the optical collection system.

2. The capillary of claim 1 wherein the cross-sectional shapes defined by the outer and inner wall surfaces are triangles.

3. A capillary for use in a capillary-flow cytometer, the capillary comprising:
   a wall defining a bore extending in a longitudinal direction, the wall further comprising:
   an outer wall surface defining a cross-sectional shape of the wall, the cross-sectional shape of the wall being traverse to the longitudinal direction and selected from the group consisting of a hemisphere and a rhomboid; and
   a substantially non-reflective inner wall surface defining a cross-sectional shape of the bore, the shape of the bore being traverse to the longitudinal direction of the bore and selected from the group consisting of a trapezoid and a triangle;

wherein the capillary is configured so that upon installation in a capillary-flow cytometer, substantially all light collected by an optical collection system of the capillary-flow cytometer passes through a side of the outer wall surface that is closest to the optical collection system.

4. A capillary-flow cytometer comprising:
a capillary comprising a wall having inner and outer wall surfaces and extending in a longitudinal direction, the inner wall surface defining a bore also extending in the longitudinal direction and having a cross-sectional shape lacking point symmetry;
a fluidics system for creating a pressure differential in the bore in the longitudinal direction and transporting a particle-containing sample fluid through the capillary;
an excitation optical system configured for illuminating a portion of the capillary;
an optical collection system configured for collecting light from the sample fluid as it travels through the illuminated portion capillary;
an optical detector configured for detecting light collected by the optical collection system; and
a data acquisition and analyzer system for analyzing signals from the optical detector;
wherein the capillary is configured so that substantially all light collected by the optical collection system passes through an area of the outer wall surface of the capillary that is closest to the optical collection system and the inner wall surface is substantially non-reflective.

5. The capillary-flow cytometer of claim 4 wherein a cross-sectional shape defined by the outer wall surface of the capillary and traverse to the longitudinal direction of the wall is of the same shape as the cross-sectional shape defined by the inner wall surface of the capillary.

6. The capillary-flow cytometer of claim 5 wherein the cross-sectional shapes defined by the outer and inner wall surfaces of the capillary are triangles.

7. The capillary-flow cytometer of claim 4 wherein a cross-sectional shape defined by the outer wall surface of the capillary and traverse to the longitudinal direction of the wall differs in shape from the cross-sectional shape defined by the inner wall surface of the capillary.

8. The capillary-flow cytometer of claim 7 wherein the cross-sectional shape defined by the outer wall surface of the capillary is a rectangle; and
wherein the cross-sectional shape defined by the inner wall surface of the capillary is a trapezoid.

9. The capillary-flow cyrometer of claim 7 wherein the cross-sectional shape defined by the outer wall surface of the capillary is a rectangle; and
wherein the cross-sectional shape defined by the inner wall surface of the capillary is a triangle.

10. The capillary-flow cytometer of claim 7 wherein the cross-sectional shape defined by the outer wall surface of the capillary is a triangle; and
wherein the cross-sectional shape defined by the inner wall surface of the capillary is a trapezoid.

11. The capillary-flow cytometer of claim 7 wherein the cross-sectional shape defined by the outer wall surface of the capillary is selected from the group consisting of a hemisphere and a rhomboid; and
wherein the cross-sectional shape defined by the inner wall surface of the capillary is selected from the group consisting of a trapezoid and a triangle.

12. The capillary-flow cytometer of claim 4 wherein the inner wall surface of the capillary is tilted with respect to an axis of the optical collection system so that a widest dimension of the bore of the capillary is closest to the optical collection system.

13. A capillary flow cytometer comprising:
a capillary having a wall extending in a longitudinal direction to define a bore for supporting flow of a particle-containing sample fluid, the wall having inner and outer wall surfaces, the inner wall surface defining a cross-sectional shape of the bore such that the cross-sectional shape lacks point symmetry;
a fluidics system that transports the particle-containing sample fluid through the bore through the creation of a fluid pressure differential;
an excitation optical system for passing light through a first side of the capillary wall and illuminating the sample fluid as it passes through a portion of the capillary;
an optical collection system for collecting light from the illuminated sample fluid, wherein substantially all of the collected light passes through a second side of the wall;
an optical detector for detecting light collected by the optical collection system; and
a data acquisition and analyzer system for analyzing signals from the optical detector.

14. The flow cytometer of claim 13 wherein the excitation light is substantially transmitted by the first side of the wall.

15. The capillary of claim 13 in which the wall is formed from a material that is selected from the group consisting of glass, plastic and fused silica.

16. The capillary of claim 13 wherein the second side has a shape that is a section of a geometric figure selected from the group consisting of a circle, a parabola, and an ellipse.

17. A capillary for use in a capillary-flow cytometer, the capillary comprising:
a wall defining a bore extending in a longitudinal direction, the wall further comprising:
an outer wall surface having a side, the side having a shape that is a section of a geometric figure selected from the group consisting of a circle, a parabola, and an ellipse; and
a substantially non-reflective inner wall surface defining a cross-sectional shape of the bore, the cross-sectional shape of the bore being traverse to the longitudinal direction and lacking point symmetry;
wherein the capillary is configured so that upon installation in a capillary-flow cytometer with the side of the outer wall surface closest to an optical collection system of the capillary-flow cytometer, substantially all light collected by the optical collection system passes through the side.

18. A capillary for use in a capillary-flow cytometer, the capillary comprising:
a wait defining a bore extending in a longitudinal direction, the wall further comprising:
a substantially non-reflective inner wall surface defining a trapezoidal cross-sectional shape of the bore traverse to the longitudinal direction; and
an outer wall surface defining a triangular cross-sectional shape of the wall traverse to the longitudinal direction;
wherein the capillary is configured so that upon installation in a capillary-flow cytometer, substantially all light collected by an optical collection system of the capillary-flow cytometer passes through a side of the outer wall surface that is closest to the optical collection system.

* * * * *